(12) United States Patent
Pearson Peyton (10) Patent No.: US 9,047,664 B2
(45) Date of Patent: Jun. 2, 2015

(54) APPARATUS AND METHOD FOR UTILIZING MAMMOGRAM IMAGES FOR VERIFICATION

(71) Applicant: Kathryn Pearson Peyton, Jacksonville, FL (US)

(72) Inventor: Kathryn Pearson Peyton, Jacksonville, FL (US)

( * ) Notice: Subject to any disclaimer, the term of this patent is extended or adjusted under 35 U.S.C. 154(b) by 77 days.

(21) Appl. No.: 13/907,702

(22) Filed: May 31, 2013

(65) Prior Publication Data

US 2014/0355840 A1    Dec. 4, 2014

(51) Int. Cl.
*G06K 9/00* (2006.01)
*G06T 7/00* (2006.01)

(52) U.S. Cl.
CPC .......... *G06T 7/0014* (2013.01); *G06K 9/00362* (2013.01)

(58) Field of Classification Search
CPC .................. G06T 2207/30068; G06T 7/0012; G06T 2207/10116; G06T 15/08; G06T 19/20; G06T 2200/04; G06T 2207/10028; G06T 2207/20044; G06T 2219/2016; G06T 7/608; G06T 7/0081; G06T 2207/10081; G06T 2207/10124; G06T 2207/30096; G06T 7/0024; A61B 6/502; A61B 6/463; A61B 8/0825; A61B 6/5247; A61B 8/406; A61B 8/463; A61B 8/5238; A61B 5/055; A61B 6/03; A61B 6/482; A61B 6/545; A61B 5/1075; A61B 5/4312; G06K 2209/05; G06K 9/00362; Y10S 128/92; Y10S 128/922; Y10S 128/923; G06F 19/321; G06F 9/3406; G06F 19/3431; G06F 19/345; G06Q 50/24; G01N 33/57415
USPC .................................................. 382/115, 134
See application file for complete search history.

(56) References Cited

U.S. PATENT DOCUMENTS

2006/0110018 A1* 5/2006 Chen et al. ..................... 382/130
2007/0061393 A1* 3/2007 Moore ........................... 709/201
2009/0086891 A1* 4/2009 Ofuji ............................... 378/37
2009/0257657 A1* 10/2009 Temmermans et al. ........ 382/195
2010/0067769 A1* 3/2010 Neemuchwala et al. ..... 382/132

* cited by examiner

*Primary Examiner* — Edward Park
(74) *Attorney, Agent, or Firm* — Arlyn Alonzo; Alonzo & Associates (57) ABSTRACT

A method and apparatus for utilizing mammogram images for verification, including obtaining one or more mammogram image of a patient; determining a first set of breast characteristics from the one or more mammogram image, wherein the first set of breast characteristics include breast landmark, breast tissue density, tissue pattern and breast finding; comparing the first set of breast characteristics with a second set of breast characteristics to yield a comparison, wherein the second set of breast characteristics is from one or more previous mammogram image identified as potentially belonging to the patient using an identification not related to content of a mammogram image; and determining based on the comparison whether the one or more previous mammogram image belongs to the patient.

18 Claims, 10 Drawing Sheets

| | 5 | | | | | | | | | |
|---|---|---|---|---|---|---|---|---|---|---|
| | 4 | | | | | | | | | |
| | 3 | | | | | | | | | |
| | 2 | | | | | | | | | |
| | 1 | | | | | | | | | |
| NIPPLE | 0 | | | | | | | | | |
| | -1 | | | | | | | | | |
| | -2 | | | | | | | | | |
| | -3 | | | | | | | | | |
| | A | B | C | D | E | F | G | H | I | J |

APPARATUS AND METHOD FOR UTILIZING MAMMOGRAM IMAGES FOR VERIFICATION

FIELD

This disclosure relates generally to apparatus and methods for utilizing mammogram images. More particularly, the disclosure relates to utilizing mammogram images for computerized comparison and verification.

BACKGROUND

Women over a certain age routinely have mammogram images of their breast taken as a screening and diagnostic tool for detecting early breast cancer. Throughout a woman's lifetime, she may have many mammogram images taken. The interpretation of these mammograms relies heavily on comparison with prior mammograms. Historically, a tremendous amount of effort is expended in obtaining prior mammogram images as patients may have their mammogram images performed by multiple doctors, in different facilities, and in various geographical locations over the patient's recommended mammographic evaluation age. Hospitals and outpatient imaging centers may spend significant time and money tracking and compiling prior patient records ((some may not be) often not recalled by the patient), creating discs and mailing discs of the mammogram images, and/or downloading vendor-specific and incompatible images from discs into Picture Archiving and Communication System (PACS) (with an approximate estimated cost of $30 per patient). Without prior reference mammogram images, for example, approximately 20% of women may undergo additional unnecessary and expensive diagnostic mammogram and/or ultrasound imaging. And, in some cases, patients are subjected to additional follow-up(s), unnecessary radiation, biopsies, expense(s) and anxiety. Thus, it is desirable that mammogram images be readily available for comparison, as in cloud storage, with current mammogram images utilized in verification of a patient's identity by matching with her prior mammogram images.

SUMMARY

The following presents a simplified summary of one or more aspects in order to provide a basic understanding of such aspects. This summary is not an extensive overview of all contemplated aspects, and is intended neither to identify key or critical elements of all aspects nor delineate the scope of any or all aspects. Its sole purpose is to present some concepts of one or more aspects in a simplified form as a prelude to the more detailed description that is presented later.

Disclosed is an apparatus and method for utilizing mammogram images for verification. According to one aspect, a method for utilizing mammogram images for verification, including obtaining one or more mammogram images of a patient; performing one or more of the following on the one or more mammogram images: a) analyze nipple, skin line, and pectoralis muscle for assessment of size and shape of a breast or pair of breasts of the patient and generating a first analysis result; b) analyze breast density and glandular pattern of the breast or pair of breasts of the patient and generating a second analysis result; c) analyze at least one breast landmark and corresponding coordinate location of the at least one landmark and generating a third analysis result; or d) analyze a region of greatest breast tissue density of the breast or pair of breasts of the patient and generating a fourth analysis result; comparing one or more of the following to yield a comparison: the first analysis result, the second analysis result; the third analysis result or the fourth analysis result with one or more previous mammogram image, wherein the one or more previous mammogram is identified as potentially belonging to the patient using an identification not related to content of a mammogram image; creating a match probability based on the comparison; and determining whether the one or more previous mammogram image belong to the patient using the match probability.

According to another aspect, a method for utilizing mammogram images for verification, including obtaining one or more mammogram image of a patient; determining a first set of breast characteristics from the one or more mammogram image, wherein the first set of breast characteristics include breast landmark, breast tissue density, tissue pattern and breast finding; comparing the first set of breast characteristics with a second set of breast characteristics to yield a comparison, wherein the second set of breast characteristics is from one or more previous mammogram image identified as potentially belonging to the patient using an identification not related to content of a mammogram image; and determining based on the comparison whether the one or more previous mammogram image belongs to the patient.

According to another aspect, an apparatus including a processor and a memory, the memory containing program code executable by the processor for performing the following: obtaining one or more mammogram image of a patient; performing one or more of the following on the one or more mammogram image: a) analyze nipple, skin line, and pectoralis muscle for assessment of size and shape of a breast or pair of breasts of the patient and generating a first analysis result; b) analyze breast density and glandular pattern of the breast or pair of breasts of the patient and generating a second analysis result; c) analyze at least one breast landmark and corresponding coordinate location of the at least one landmark and generating a third analysis result; or d) analyze a region of greatest breast tissue density of the breast or pair of breasts of the patient and generating a fourth analysis result; comparing one or more of the following to yield a comparison: the first analysis result, the second analysis result; the third analysis result or the fourth analysis result with one or more previous mammogram image, wherein the one or more previous mammogram is identified as potentially belonging to the patient using an identification not related to content of a mammogram image; creating a match probability based on the comparison; and determining whether the one or more previous mammogram image belong to the patient using the match probability.

According to another aspect, an apparatus including a processor and a memory, the memory containing program code executable by the processor for performing the following: obtaining one or more mammogram image of a patient; determining a first set of breast characteristics from the one or more mammogram image, wherein the first set of breast characteristics include breast landmark, breast tissue density, tissue pattern and breast finding; comparing the first set of breast characteristics with a second set of breast characteristics to yield a comparison, wherein the second set of breast characteristics is from one or more previous mammogram image identified as potentially belonging to the patient using an identification not related to content of a mammogram image; and determining based on the comparison whether the one or more previous mammogram image belongs to the patient.

By matching current mammograms with prior mammograms unique to that individual patient, a patient's prior historical record of mammogram images may be securely released for viewing and image interpretation.

Advantages of the present disclosure may include improved quality of care and patient outcomes; reduced healthcare costs for patients, providers, and payers (e.g., insurance carrier); and improved and secured release of universally accessible and patient portable prior mammogram images.

It is understood that other aspects will become readily apparent to those skilled in the art from the following detailed description, wherein it is shown and described various aspects by way of illustration. The drawings and detailed description are to be regarded as illustrative in nature and not as restrictive.

DETAILED DESCRIPTION

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for the purpose of providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the present disclosure.

While for purposes of simplicity of explanation, the methodologies are shown and described as a series of acts, it is to be understood and appreciated that the methodologies are not limited by the order of acts, as some acts may, in accordance with one or more aspects, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with one or more aspects.

Unlike other types of medical imaging, mammography relies heavily on comparisons with prior mammograms to determine what is normal or an early sign of breast cancer. Because breast tissue is unique to each individual, archived images provide a benchmark for evaluating changes in tissue composition and assist in the early detection of cancer. An improved chance for accurate diagnosis is to have a patient's entire dossier of prior mammogram images on-hand to accurately detect the incremental changes that can indicate breast cancer. Without access to a history of the patient's mammogram images, the detection and cure of breast cancer may be far more complex for the caregiver.

In one aspect, mammogram images may be used for verification for release of prior mammogram images, for example, to medical personnel. In one example, utilizing mammogram image for verification may enable a medical technologist to access and verify prior mammogram images from a storage system (e.g., a cloud storage). Having access to a patient's prior mammogram images may improve the accuracy in interpretation of current mammogram images taken of the patient. Having access to the patient's complete history of mammogram images may help with earlier detection of breast cancer and may reduce the need for additional unnecessary mammogram images to be taken.

In one example, a patient's mammogram image is analyzed utilizing a set of breast characteristics which may include one or more of the following: breast landmarks, breast tissue densities, tissue patterns, breast findings and other distinguishing features to generate a probabilistic signature that is used to verify that prior mammogram images belong to the same patient. For example, current mammogram images are compared with stored prior mammogram images of patients queried under name and birthdate. A probabilistic match is calculated and a reasonable "match" is determined to provide a desirable level of secure release of a patient's medical records and mammogram images. In one example, once there is verification that prior mammogram images belong to the same patient, then access to these prior mammogram images may be given to the requesting medical personnel.

In one example, breast landmarks may include nipples, pectoralis muscle, skin lines for breast size, shape or contour of the breast, for example, with calculation of measurements of posterior nipple line depth and estimated width and height of breast. In one example, breast tissue densities may include fatty tissue, fibroglandular tissue, other soft tissues (e.g., blood vessels, lymph nodes, noncalcified masses), calcifications, and artifact-related metallic densities. In one example, breast tissue densities are used for calculation of overall tissue density which is used for comparison between mammogram images.

In one example, tissue patterns (e.g., Glandular tissue pattern) may be matched by computer analysis of swirls, lines and tubules, arcs, dots, as well as other categories of texture analysis of mammographic parenchymal patterns. In one example, breast findings may include lymph nodes, blood vessels, noncalcified or calcified masses, calcifications, metallic clips, skin lesions. In one example, the other distinguishing features may include surgical or biopsy clips, implants, skin lesions or artifacts (e.g., tattoos).

In one aspect, a universal, secure and accessible cloud storage system of prior mammogram images is provided. For example, advances in cloud technology and implementations of robust Electronic Medical Record (EMR) systems are intersecting in a way that represents an optimum time to implement a cloud storage system for mammogram images. In one statistic, it appears that this is a market with a large user base of approximately 74 million women undergoing 48 million mammogram sessions a year (approximately 55% of the mammographic age market).

While the technology for cloud storage and image sharing network exists, it is not centralized nor connected, and the secure release of these images and records is of upmost concern. Currently, secure access to a patient's medical records may involve some form of authentication and authorization with passwords. However, passwords or other authentication questions and answers are frequently not recalled by patients. Biomarkers such as fingerprints, retinal scans, and electronic signatures have also been used for secure access to stored information as well as utilized for secure release of medical records. As mammograms are being performed for current evaluation anyway, the current mammogram may be utilized as an alternative for release of prior records, easily implemented in all facilities without additional biomarker scan equipment.

A mammogram image of a person's breast is as unique to an individual as a person's face, and therefore a mammogram image may serve as a unique patient identifier, similar to other biomarkers such as fingerprint or retinal scan. The mammogram patient identifier may be used, for example, to securely release prior mammogram images from a cloud storage by using patient's current mammogram to "match" with prior mammogram images of that patient in the cloud storage. That is, a patient's current mammogram images are compared with prior stored mammogram images using a set of analyzed characteristics and calculated probabilistic match. If the probabilistic match is greater than a set threshold, then there is authorization for release of stored mammogram images to the requesting medical personnel. This operation would allow for secure release of mammogram images and other medical records from a cloud storage. Although the examples herein are presented with the concept of a cloud storage, one skilled in the art would understand that any type of storage system (in addition to a cloud storage) is within the scope and spirit of the present disclosure. In one example, matching of mammogram images may ultimately be utilized in computer-aided detection algorithms in order to have computer assessment of interval changes that may indicate the earliest changes of breast cancer.

Figure 1:
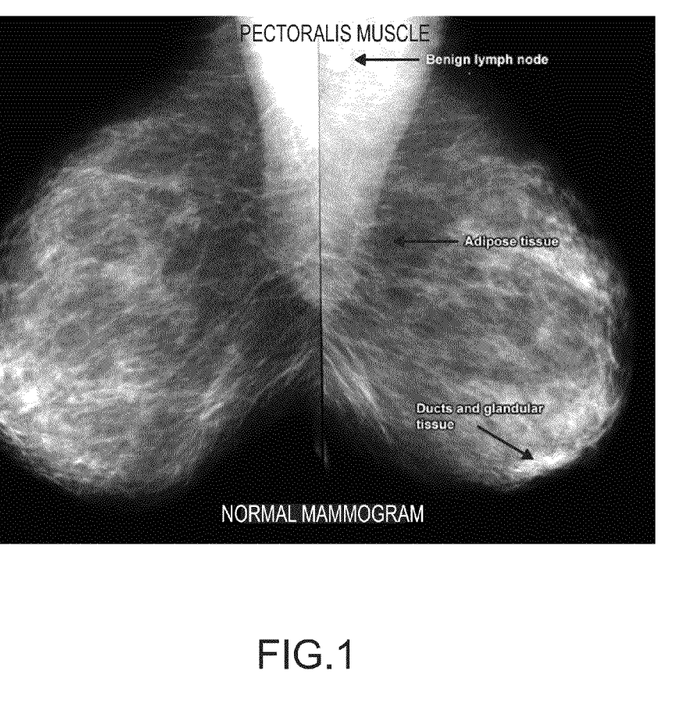
FIG. 1 illustrates an example of a normal mammogram image.

FIG. 1 illustrates an example of a normal mammogram image. In FIG. 1, the pectoralis muscle is shown, along with the adipose tissue and some ducts and glandular tissue. In the example of FIG. 1, a benign lymph node is visible. FIG. 1 illustrates an image of normal, that is, breast cancer free, right and left breasts of a patient.

The mammogram is a radiographic image composed of varying shades of grey to white depending on different tissue densities of the breast. The tissue densities range from fatty tissue (grey) to fibroglandular tissue (varying shades of white), as well as soft tissues (lighter white) to calcifications (bright white) and metallic densities (extremely bright white). In mammogram image, air is black.

Figure 2:
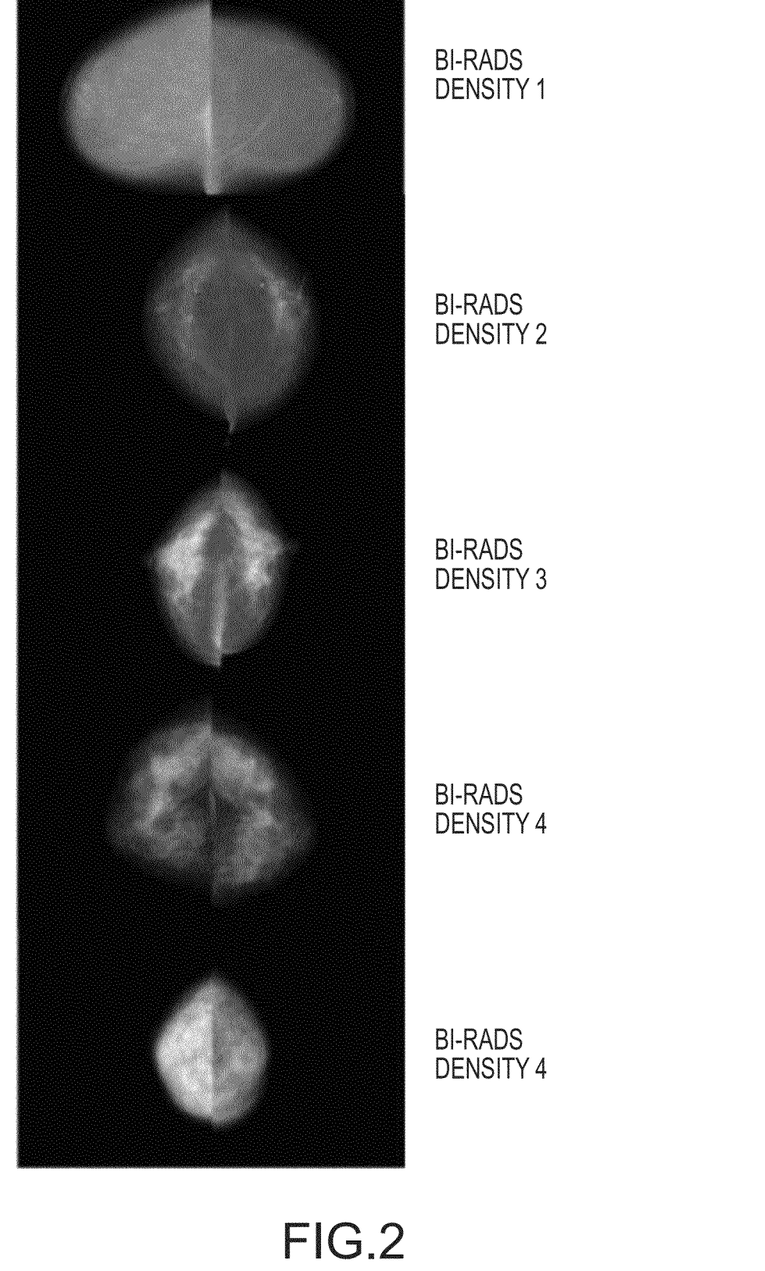
FIG. 2 illustrates five examples of breast pairs with varying breast densities.

FIG. 2 illustrates five examples of breast pairs with varying breast densities. Breast density is a measure for describing the proportion of fibroglandular tissue to fat in the breast. That is, breast tissue density descriptors are based on the proportion of fibroglandular tissue to fat. Breast density is described in the Breast Imaging Reporting and Data Systems (BI-RADS) lexicon as follows:

"Extremely dense" (>75% fibroglandular tissue)
"Heterogeneously dense" (50-75% fibroglandular tissue)
"Scattered fibroglandular densities" (25-50% fibroglandular tissue)
"Almost entirely fatty" (<25% fibroglandular tissue)

Figure 3:
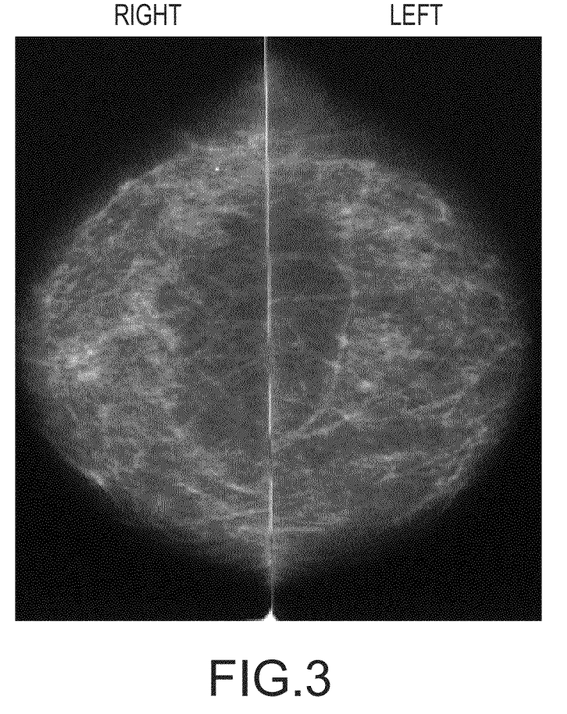
FIG. 3 illustrates an example of a craniocaudal (CC) view of a pair of breasts.
Figure 4:
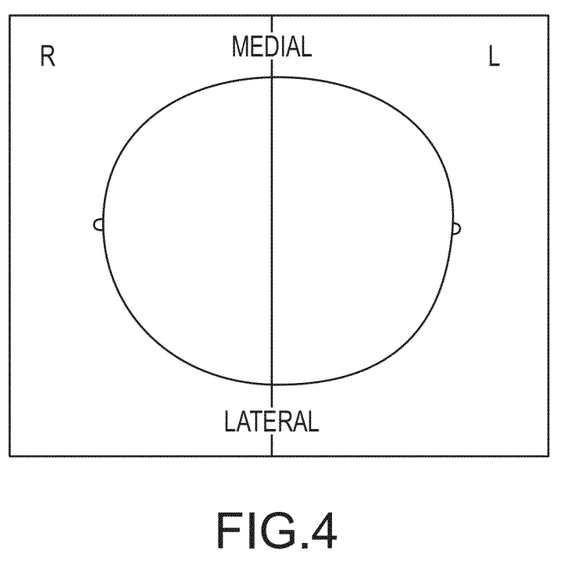
FIG. 4 illustrates an example of the breast outline of the craniocaudal (CC) view depicted in FIG. 3.
Figure 5:
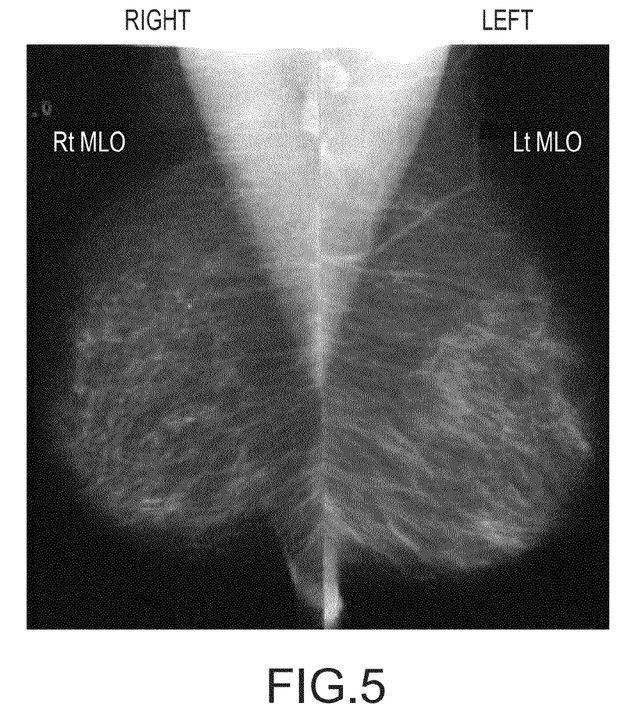
FIG. 5 illustrates an example of a Mediolateral Oblique (MLO) view of a pair of breasts.
Figure 6:
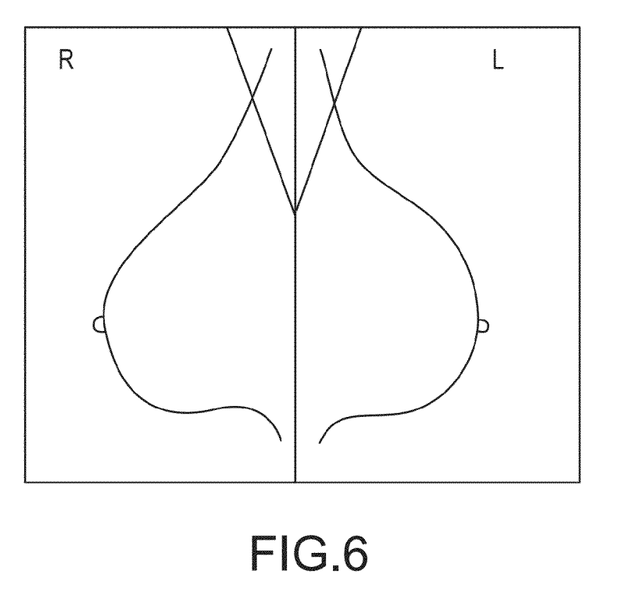
FIG. 6 illustrates an example of the breast outline of the Mediolateral Oblique (MLO) view depicted in FIG. 5.

The images for a breast screening exam are typically obtained in two projections: Craniocaudal (CC) (0 degree angle relative to vertical, imaged from head to toe) and Mediolateral Oblique (MLO) (varying obliquities usually between 45-60 degrees, imaged from inner to outer). FIG. 3 illustrates an example of a craniocaudal (CC) view of a pair of breasts. FIG. 4 illustrates an example of the breast outline of the craniocaudal (CC) view depicted in FIG. 3. FIG. 5 illustrates an example of a Mediolateral Oblique (MLO) view of a pair of breasts. FIG. 6 illustrates an example of the breast outline of the Mediolateral Oblique (MLO) view depicted in FIG. 5.

Although Craniocaudal (CC) and Mediolateral Oblique (MLO) views are the most frequently used for mammogram images, additional images may be obtained for diagnostic mammogram, including True Lateral (90 degree angle) views, spot compression magnification views (all projections), rolled views, tangential views, and step-oblique images (differing obliquities). For example, for patients with breast implants, image views may include CC and MLO views and/or some additional views to be taken with the implants in their typical position. And, image views may also include CC and MLO views and/or some additional views to be taken with the implants displaced (i.e., pushed back). Matching of CC views or implant-displaced CC views are the most likely to match and be reproducible from year to year, however the MLO views may be matched as deemed necessary, particularly for volume density analysis.

A patient's mammogram images may vary minimally from year to year. Some changes are attributable to hormonal changes and/or loss of glandular density with age. Calcifications may gradually form within blood vessels of a breast to change mammogram images. Growth or formation of benign masses such as fibroadenomas may also contribute to changes in a patient's mammogram images. Trauma and/or injury to the breast in between mammogram procedures may also change the mammogram images.

Therefore, "matching" of mammogram images with prior mammogram images may not be exact and may be approximated with, for example, an approximate 90% match in order for "release of images" from storage. In one example, when a discrepancy occurs with a queried patient's mammogram images not matching, an option may be to manually download the mammogram images and visually confirm match of the patient's current mammogram images with prior mammogram images to confirm that the prior mammogram images also belong to the same patient. Mammogram images of patients undergoing significant body changes (for example, due to tremendous weight gain or loss, breast surgery, or development of a large tumor or cancer) may not "match" with their prior mammogram images. In these cases, with a patient's permission, a medical personnel or technologist may manually release a patient's prior images.

An example process of matching mammogram images may include matching one or more of the following: breast landmarks, breast tissue densities, tissue patterns, breast findings and other distinguishing features. For example, matching breast landmarks may include matching nipples, pectoralis muscle, skin lines for breast size, shape or contour of the breast. The matching may include calculating the posterior nipple line depth and estimating the width and the height of breast.

Figure 7:
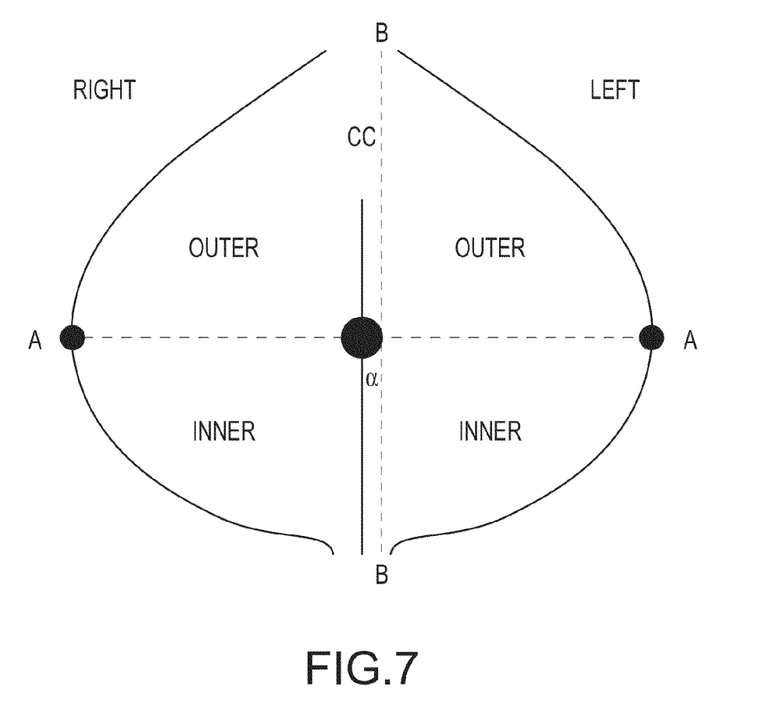
FIG. 7 illustrates an example of a craniocaudal (CC) view with measurement of depth and width of the breasts.

FIG. 7 illustrates an example of a craniocaudal (CC) view with measurement of depth and width of the breasts. In one example, take depth and width measurements using a Craniocaudal (CC) image. Measure the depth of the breast in centimeters. In one example, line AA in FIG. 7 indicates the depth. The depth may be defined as the horizontal measurement of the nipple to the pectoralis muscle border or to the posterior margin of the mammogram image. And, measure the width of the breast in centimeters. The width is defined as the vertical measurement of outer skin line to inner skin line at its greatest width. In one example, line BB in FIG. 7 indicates the width. In one example, assess as a "match" if both depth and width measurements are within +/−3 cm.

Figure 8:
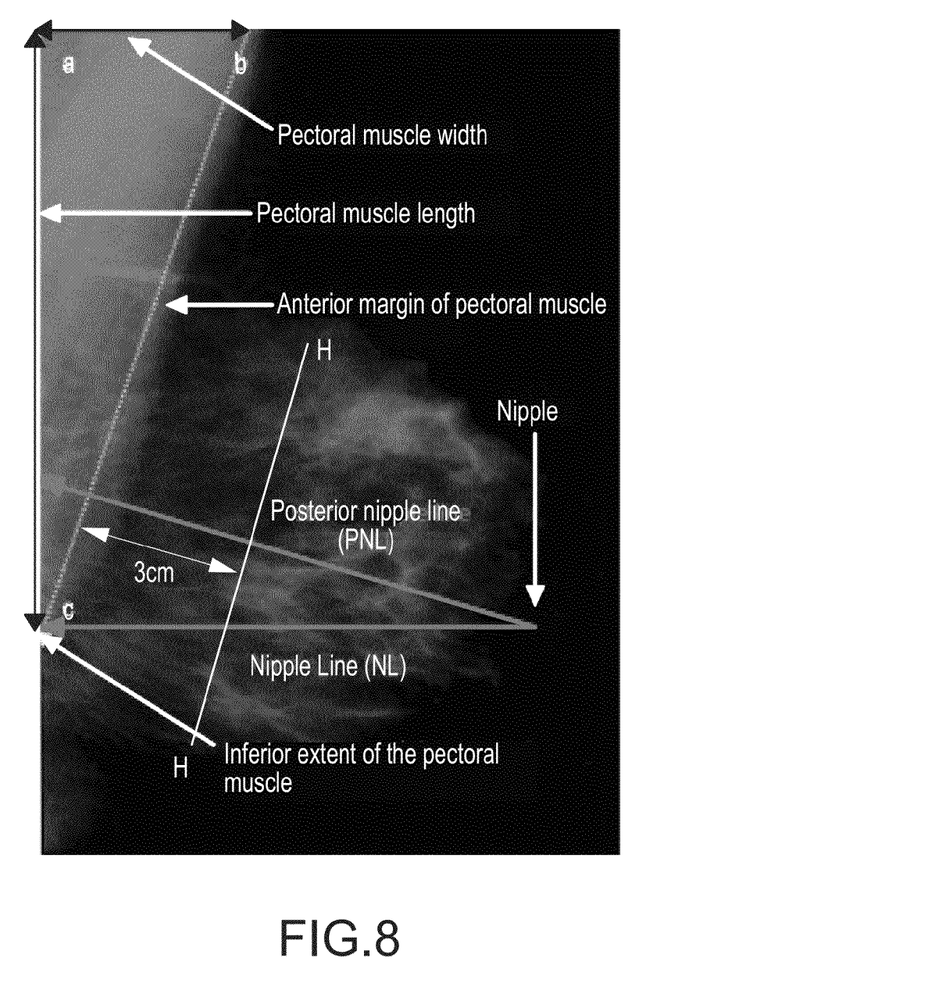
FIG. 8 illustrates an example of a Mediolateral Oblique (MLO) view with measurement of the posterior nipple line.

FIG. 8 illustrates an example of a Mediolateral Oblique (MLO) view with measurement of the posterior nipple line. The measurement of the posterior nipple line is the distance of the depth of the posterior nipple line (PNL) to the pectoralis muscle, measured for example in centimeters. The posterior nipple line (PNL) refers to a line drawn tangentially posteriorly from the nipple towards the pectoral muscle on the mammogram as shown in FIG. 8.

In one example, measure an estimated "height" of a breast on a MLO view by measuring the superior skin line to the inferior skin line along the perpendicular line drawn at a point designated on the PNL. In one example, the PNL is measured in centimeters. The estimated "height" (indicated as HH in FIG. 8) is the length of the line (measured in centimeters from skin to skin) perpendicular to the PNL drawn 3 cm anterior to the pectoralis muscle line along the PNL line in the direction toward the nipple. The line HH in FIG. 8 indicates the height.

Figure 9:
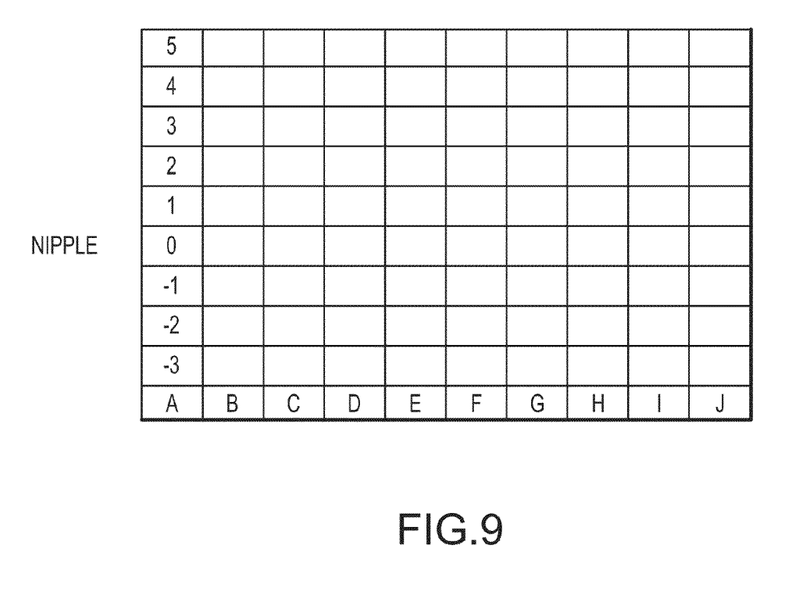
FIG. 9 illustrates an example of a coordinate system for mapping a mammogram image.

In one example, a coordinate system for mapping may be used. FIG. 9 illustrates an example of a coordinate system for mapping a mammogram image. In one example, the coordinate system superimposed on mammogram image with nipple at 0. Mapping of each square is done for, for example, breast tissue density and breast landmarks for comparison with prior mammogram image coordinates. The coordinate system may be established based on X/Y coordinates beginning at the nipple and separated by 1 centimeter (cm) or smaller lines.

In one example, a craniocaudal (CC) view is used. The vertical columns of the coordinate system are labeled with letters, for example, A through J as shown in FIG. 9. Each square (i.e., each letter) represents a unit of depth of the breast. In one example, in the horizontal direction, each square (i.e., each letter) represents 1 centimeter square ($cm^2$). In one example, the horizontal rows are labeled with numbers. "0" represents the location of the nipple. The positive numbers above the nipple "0" indicates a unit of height above the nipple and the negative numbers below the nipple "0" indicates a unit of height below the nipple. In one example, in the vertical direction, each square (i.e., each number) represents 1 centimeter square ($cm^2$).

In one example, a Mediolateral Oblique (MLO) view is used. In the MLO view, the vertical columns are labeled in letters, for example, A through J. Each letter represents a unit of depth of the breast at a posterior margin of the mammogram image. The horizontal rows are labeled in numbers with "0" indicating the position of the nipple. The positive numbers above the nipple "0" indicates a unit of width to one side of the nipple and the negative numbers below the nipple "0" indicates a unit of width to the other side of the nipple.

Each square therefore represents one centimeter square ($cm^2$) of area that may be used as a coordinate for comparison and matching. In one example, the acceptable tolerance is +/−3 adjacent squares in all directions.

The coordinate system may be utilized for quantitative image analysis of region of interest of the breast. For example, assume a patient's left breast includes a lymph node (which could be round, ovoid, kidney-bean shaped nodule) and is usually found in axilla and Upper Outer Quadrant (UOQ). Compare the location of the lymph node in the current mammogram image with that of a previous mammogram image that may belong to the patient. That is, determine if the distance from the nipple to the lymph node is +/−3 cm (or in X/Y coordinate determine if it is within 3 adjacent squares) between the current mammogram image and the previous mammogram image. If yes, determine that on this point, there is a match. Although lymph node location in a coordinate system is used herein as an example, one skilled in the art would understand that other characteristics of the breast may be compared using the coordinate system. Some examples, although not an exclusive list, may include blood vessels, noncalcified masses, calcified masses, pectoralis muscle location, etc.

An example process of matching mammogram images may include matching breast tissue densities. In one example, the breast tissue density is a measure of the fibroglandular tissue proportion to fat in the breast. Glandular Tissue appears similar to "white clouds" on mammogram images. In one example, the breast density is the measure of the brightness of the "clouds" (e.g., scaled 1-10) and percent of area involved (%). And, the rating of the breast density (e.g., extremely dense, heterogeneously dense, scattered fibroglandular density or almost entirely fatty) is based on the percentage of fibroglandular tissue present in the breast. Analysis of the breast density may be done with a craniocaudal (CC) view and/or a Mediolateral Oblique (MLO) view, compared separately in 2-D views or eventually through 3-D volume calculations. In one example, the breast density index is matched with positions of the highest density based on the coordinate system. That is, a first coordinate system may be used to record the locations of the varying breast densities in a current set of mammogram images and then compared to a second coordinate system used to record the locations of the varying breast densities in a previous set of mammogram images. Comparison of the first and second coordinate system is then used to determine if the two sets of mammogram images belong to the same patient.

Figure 10:
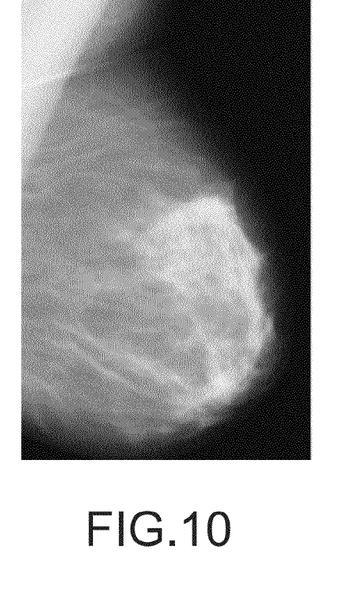
FIG. 10 illustrates an example of Mediolateral Oblique (MLO) view of a breast.
Figure 11:
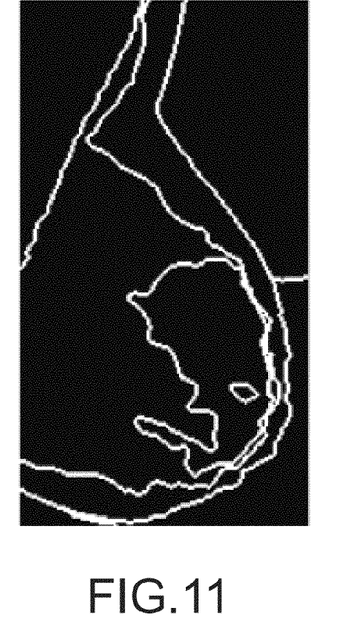
FIG. 11 illustrates an example of a line analysis of prominent fibroglandular tissue patterns in the breast of FIG. 10.

An example process of matching mammogram images may include matching tissue patterns. FIG. 10 illustrates an example of Mediolateral Oblique (MLO) view of a breast. FIG. 11 illustrates an example of a line analysis of prominent fibroglandular tissue patterns in the breast of FIG. 10. The locations of prominent fibroglandular tissue patterns (for example, as indexed using a coordinate system) are compared between mammogram images to determine if the different mammogram images belong to the same patient. Also, for example, the presence or absence of glandular tissue density behind the nipple or in inner breast may be matched, and comparisons from different mammogram images may be used to determine if the different mammogram images belong to the same patient. Although a Mediolateral Oblique (MLO) view is used in this example, one skilled in the art would understand that other views of a mammogram image, for example, a craniocaudal (CC) view may be used without deviating from the scope or spirit of the present disclosure.

In one example, swirls of the breast are matched. That is, lines depicting tubules or ducts, arcs and/or dots that represent breast tissue patterns are matched. For example, a series of features (e.g., using mathematical descriptors) may be extracted from each region of interest (ROI) of the breast to characterize the mammographic parenchymal pattern. And, comparisons from the different mammogram images may be made to determine if the different mammogram images belong to the same patient. In another example, the edge of the fibroglandular complex where fat tissue interfaces with the glandular tissue under the skin line as well as in posterior aspect of breast is matched, for example, using the coordinate system to determine whether the edge in one mammogram image matches the edge in another mammogram image to determine if the two mammogram images belong to the same patient.

An example process of matching mammogram images may include matching breast findings which may include lymph nodes, blood vessels, noncalcified or calcified masses, calcifications, metallic clips, skin lesions. Locations of these breast findings in a first mammogram image may be indexed on a first coordinate system. A second coordinate system may index breast findings that appear in a second mammogram image. The two coordinate systems may be compared to determine if the locations of the breast findings and the types of breast findings match within a threshold (e.g., within 3 cm). If there is sufficient matching, then determine that the two mammogram images belong to the same patient. In one example, the first and second mammogram images are taken at different times, maybe even years apart.

An example process of matching mammogram images may include matching other distinguishing features. The other distinguishing features may include surgical or biopsy clips, implants, skin lesions or artifacts (e.g., tattoos). Locations of these distinguishing features in a first mammogram image may be indexed on a first coordinate system. A second coordinate system may index distinguishing features that appear in a second mammogram image. The two coordinate systems may be compared to determine if the locations of the distinguishing features and the types of distinguishing features match within a threshold (e.g., within 3 cm). If there is sufficient matching, then determine that the two mammogram images belong to the same patient. In one example, the first and second mammogram images are taken at different times, maybe even years apart.

Figure 12:
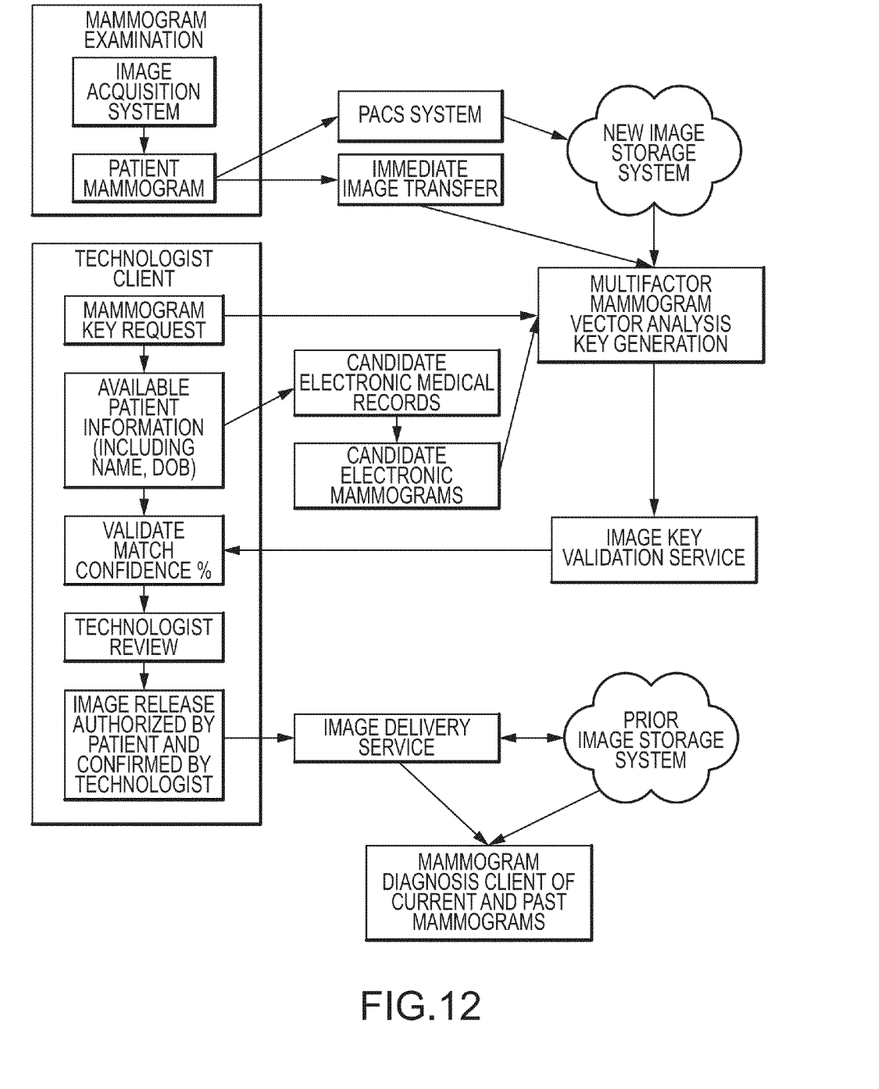
FIG. 12 illustrates an example overall flow diagram including mammogram examination, technologist client inquiries, storage of new mammogram images, retrieval of prior mammogram images, comparisons of new and prior mammogram images and diagnosis to determine if there is a match of patient identity of the new and prior mammogram images.

FIG. 12 illustrates an example overall flow diagram including mammogram examination, technologist client inquiries, storage of new mammogram images, retrieval of prior mammogram images, comparisons of new and prior mammogram images and diagnosis (e.g., via multifactor mammogram vector analysis key generation) to determine if there is a match of patient identity of the new and prior mammogram images. In one example, the steps associated with the example flow diagram in FIG. 12 may include one or more of the following. Obtain mammogram image. Auto-send the mammogram image to PACS and/or directly to cloud storage. The technologist (or medical personnel) may query the patient by name, birthdate, and facility (or city and state if facility is not recalled) of where the prior mammogram images were taken. This query, for example, may be performed using DICOM (Digital Imaging and Communications in Medicine) information stored in a cloud system. Based on these queries, mammogram images of potential matches may then be accessed for computer analysis.

In one aspect, the analysis for matching may include one or more of the following steps. One skilled in the art would understand that one or more of the steps may be enough to determine that there is a match between a new mammogram image and a previous mammogram image. The decision of how many steps must match before there is a determination that the new mammogram image and the previous mammogram image belong to the same patient may be based on various factors, such as but not limited to, how close does each step match, how reliable are the other patient information (e.g., patient name, birthdate, etc.), are there breast characteristics that do not match and are there explanations for these non-matching characteristics, etc.

One, match general breast landmarks on MLO and/or CC images (nipple, skin, pectoralis muscle, etc).

Two, assess breast size. For example, calculate breast depth along the posterior nipple line (e.g., using a MLO image) and the width of the breast (e.g., using a CC image) and determine as a match if the measurements are within +/−3 cm of each other. In one example, the measurements may be compared in centimeters. In another example, the measurements may be used to estimate the relative volume calculation of the breast in cubic centimeters ($cm^3$). And, for example, the relative breast volume calculated from the new mammogram images may be compared with the relative breast volume calculated from candidates of potential mammogram images (i.e., previous mammogram images) to determine if there's a match. A match would indicate that the new and candidates of potential mammogram images belong to the same patient.

Three, assess breast contour. For example, assign contour line along skin line for analysis of curvature (e.g., using a MLO image). In one example, the contour calculation is based on radial measurement at a point of maximal curve.

Four, analyze breast tissue density (e.g. using a MLO image and/or a CC image). In one example, an estimated "rough" calculation based on BIRADS lexicon assessed on CC and MLO views separately may be used. In one example, assess the amount of white tissue (i.e., representing fibroglandular tissues) to dark grey tissue (i.e., representing fatty tissues). Assign percentage of fibroglandular tissues relative to fatty tissues. For example, if the percentage is between 0-25%, index it as density 1. If the percentage is between 25-50%, index it as density 2. If the percentage is between 50-75%, index it as density 3. If the percentage is greater than 75%, index it as density 4. Next, match the densities at different locations of the breast using a coordinate system (e.g., as illustrated in FIG. 9). For example, assign a rating of 1 to 10 based on the brightness of white as shown in the mammogram image in each grid of the coordinate system. Comparison to a second coordinate system that represents the densities shown in a second mammogram image is then made. If there is a match of the density information of the two coordinate systems, determine that the two mammogram images may belong to the same patient.

Five, assign computer-generated lines to prominent parenchymal patterns and compare the prominent parenchymal patterns from the new mammogram image with the prominent parenchymal patterns from the prior mammogram image to determine if there's a match.

Six, assign grid coordinate system to CC and/or MLO projections and register specific landmarks within each coordinate. These coordinates plus/minus a predetermined region of error are then compared with prior image coordinates. In one example, set the area size of each coordinate as 1 centimeter (cm). Thus, each square in the coordinate system would represent an area of 1 square centimeter ($cm^2$). Although the example sets the area size of each coordinate as 1 centimeter (cm), one skilled in the art would understand that other unit dimensions may be used without affecting the scope and/or spirit of the present disclosure. In one example, the coordinate system depicts the locations of one or more of the following in the breast: lymph nodes, distance from nipple to lymph node, blood vessels, noncalcified masses, calcified masses, and/or pectoralis muscle, etc.

Seven, assess the position of each landmark within a radial arc position from the nipple.

Based on one or more of the assessment results, calculate the probability that the new mammogram image matches the prior mammogram image. In one example, a set of multiple new mammogram images are assessed and compared with a set of multiple prior mammogram images. In one example, if the matching breast characteristics are greater than a predetermined probabilistic match, for instance 90%, then determine that the new mammogram image and the prior mammogram image belong to the same patient. And, in one example, given that there's patient identity match, authorization to release the prior mammogram image stored in a cloud storage is determined.

In one example, if there is no match, the technologist (or medical personnel) may query the patient to determine if there has been body changes (e.g., interval surgery, significant weight change, interval development of large mass, adding of artifacts, etc.) between the time the prior mammogram image and the new mammogram image was taken that could affect the matching process.

In one example, even if the matching does not meet a fixed threshold (e.g., 90% matching criteria), with specific patient authorization, the technologist (or medical personnel) may manually release prior mammogram images, for example, if the prior mammogram images are reliably identified with the patient's information.

In the case where there are multiple patients with the same name, birthdate, and facility of where the prior mammogram images were taken are released from storage, then visual comparison and confirmation of match may be performed by the technologist/radiologist.

In one aspect, a mammogram examination is performed. The technologist (or medical personnel) queries prior mammogram images of similar name and birthdate. The technologist (or medical personnel) requests a matching (e.g., a computer matching) of the current mammogram images with those of selected prior mammogram images (i.e., candidates of potential mammogram images). In one aspect, the matching process may include one or more of the following: matching nipples, skin line, pectoralis muscle for assessment of size and shape of the breast; and/or matching of overall breast density, line drawings of glandular patterns. In one example, a coordinate system is used for indexing the various breast characteristics based on their respective locations. In one example, provide a coordinate system for the mammogram images to match breast landmarks and coordinate regions of breast tissue density. Based on the results of the matching process (with or without the use of the coordinate system), determine a probability of patient match to the prior mammogram images. In one example, a probability of greater than 90% is set for a patient match. In one example, if there's a patient match, authority is given for releasing the prior mammogram images from the cloud storage. In one example, if the probability is less than 90%, queries are made relating to possible patient body changes, such as but not limited to, interval surgery, significant weight changes, development of mass in the breast, adding of artifacts, etc.). In one example, manual release of prior mammogram images from the cloud storage may be authoried by the patient for visual comparison and/or confirmation by the technologist (or medical personnel).

Figure 13:
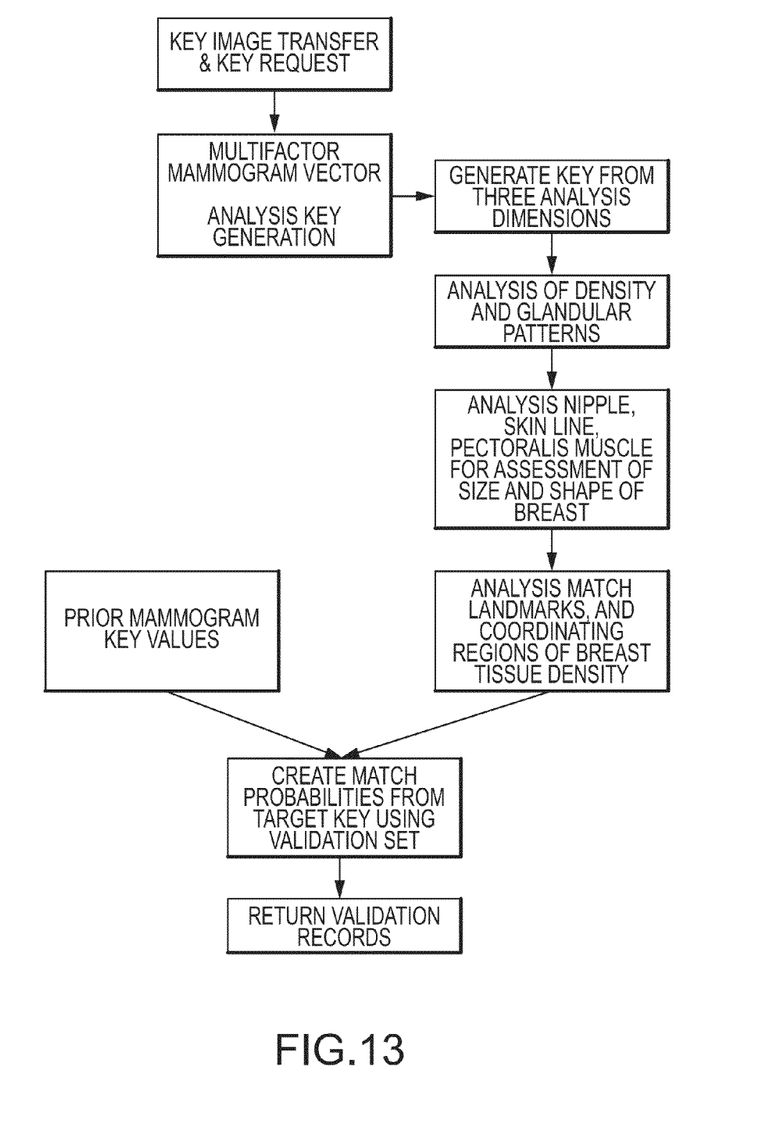
FIG. 13 illustrates an example flow diagram for matching mammogram images.

FIG. 13 illustrates an example flow diagram for matching mammogram images. In one example, the analysis for matching mammograms include a "three analysis dimensions" The "keys" are the computed values from the image analysis and are used to provide access to the images. Keys are also a common computer science term when talking about things like "key/value" databases, "record access keys", etc. The multi-factor mammogram vector analysis key generation step will create three types of keys, each representing a numeric value that can be used to compare with keys generated for other images.

First, analyze breast density and glandular patterns. Second, analyze nipple, skin line, pectoralis muscle for assessment of size and shape of the breast. Third, analyze breast landmarks and coordinate the regions of greatest breast tissue density. Once the analyses are performed, create match probabilities and use these match probabilities to validate the records. That is, if the match probabilities are high (matching "keys"), then determine that the mammogram images (new ones and prior ones) belong to the same patient.

In another example, first, analyze nipple, skin line, pectoralis muscle for assessment of size and shape of the breast. Second, analyze breast density and glandular patterns. Third, analyze breast landmarks and coordinate locations of landmarks as well as the regions of greatest breast tissue density. Once the analyses are performed, create match probabilities and use these match probabilities to validate the records. That is, if the match probabilities are high (matching "keys"), then determine that the mammogram images (new ones and prior ones) belong to the same patient. One skilled in the art would understand that the steps presented in the flow diagram may vary as to which step should precede another step and still be within the scope and spirit of the present disclosure.

In one example, mammogram images are inputted into an analysis system. Each mammogram image is calibrated against standard profiles for a mammogram image for each image source and imaging system. Adjustments between different imaging systems and even specific devices are applied to the mammogram image to make them more comparable as well as to provide a standard mammogram image for subsequent steps (e.g., the mammogram images are converted into HIE-XDS (Health Image Exchange-Cross Data Share) vendor-neutral Digital Imaging and Communication in Medicine (DICOM) format). For mammogram images that are created from imaging systems that not closely comparable, the next step is a mapping transformation system that can adjust between mammogram images to match a standard profile. The mammogram images may have grey-scale profiles, size and measurement differences. The source image may have a different structure or view of the breast. The mapping transformation system adjusts the images into standard comparison images, mapped by breast characteristics of nipple, pectoralis muscle line, and/or skin, etc. One skilled in the art would understand the breast characteristics mentioned herein are not an exclusive list and that other breast characteristics may be used in combination or separately without deviating from the scope and spirit of the present disclosure.

The next step applies image analysis, including edge and boundary analysis (parenchymal patterns), tissue types (density) and specific breast findings. Since a previous step may have adjusted the mammogram images, a mammogram image optimized to enhance boundaries may be attained. In one example, the analysis system includes filters for edge detection, or unsharp mask to create image line edges. Other techniques, such as but not limited to, scale-space or anisotropic diffusion may also be used. Tissues types may be correlated with image areas. Since tissue types have characteristic patterns and structures, these areas are selected and measured. Specific breast findings and/or other distinguishing features may also be identified with their locations also identified for exclusion or inclusion in later analysis.

In one example, the comparison step compares breast characteristics found in the different mammogram images. In one example, determine whether the relative sizes of tissue type areas correlate with each other. A probabilistic match is generated from these multiple calculated variables, allowing for release of prior secured images. The technologist or reading radiologist may then perform visual confirmation of correctly released mammogram images.

In one aspect, the mammogram images may also be compared using a distortion filter. For example, a distortion filter is applied to transform a particular breast characteristic with a test source. The amount of distortion required and the threshold degree of match of the particular breast characteristic may provide another statistical data point for comparison. In one example, additional filters may be added to increase reliability.

In one example, prior to an individual mammogram image comparison, the entire database of existing mammogram images are inputted and analyzed. These existing mammogram images provide a training corpus. For example, tests may be created that correctly match breast characteristics known to belong to the same patient are weighted more heavily. Also, tests may be created that exclude mammogram images that should not match. In one aspect, the analysis system adjusts and evolves, and may include genetic algorithms to identify comparisons that most efficiently match with sufficiently high confidence.

One skilled in the art would understand that the steps disclosed in the example flow diagrams may be interchanged in their order without departing from the scope and spirit of the present disclosure. Also, one skilled in the art would understand that the steps illustrated in the flow diagrams are not exclusive and other steps may be included or one or more of the steps in the example flow diagrams may be deleted without affecting the scope and spirit of the present disclosure.

Those of skill would further appreciate that the various illustrative components, logical blocks, modules, circuits, and/or algorithm steps described in connection with the examples disclosed herein may be implemented as electronic hardware, firmware, computer software, or combinations thereof. To clearly illustrate this interchangeability of hardware, firmware and software, various illustrative components, blocks, modules, circuits, and/or algorithm steps have been described above generally in terms of their functionality. Whether such functionality is implemented as hardware, firmware or software depends upon the particular application and design constraints imposed on the overall system. Skilled artisans may implement the described functionality in varying ways for each particular application, but such implementation decisions should not be interpreted as causing a departure from the scope or spirit of the present disclosure.

For example, for a hardware implementation, the processing units (a.k.a. processor) may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described therein, or a combination thereof. With software, the implementation may be through modules (e.g., procedures, functions, etc.) that perform the functions described therein. The software codes may be stored in memory units and executed by a processor unit. Additionally, the various illustrative flow diagrams, logical blocks, modules and/or algorithm steps described herein may also be coded as computer-readable instructions carried on any computer-readable medium known in the art or implemented in any computer program product known in the art. In one aspect, the computer-readable medium includes non-transitory computer-readable medium.

In one or more examples, the steps or functions described herein may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media may include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

In one example, the illustrative components, flow diagrams, logical blocks, modules and/or algorithm steps described herein are implemented or performed with one or more processors. In one aspect, a processor is coupled with a memory which stores data, metadata, program instructions, etc. to be executed by the processor for implementing or performing the various flow diagrams, logical blocks and/or modules described herein.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

The invention claimed is:

1. A method for utilizing mammogram images for verification, comprising:
   obtaining one or more mammogram image of a patient;
   performing one or more of the following on the one or more mammogram image:
   a) analyze nipple, skin line, and pectoralis muscle for assessment of size and shape of a breast or pair of breasts of the patient and generating a first analysis result;
   b) analyze breast density and glandular pattern of the breast or pair of breasts of the patient and generating a second analysis result;

c) analyze at least one breast landmark and corresponding coordinate location of the at least one landmark and generating a third analysis result; or
d) analyze a region of greatest breast tissue density of the breast or pair of breasts of the patient and generating a fourth analysis result;

comparing one or more of the following to yield a comparison: the first analysis result, the second analysis result; the third analysis result or the fourth analysis result with one or more previous mammogram image, wherein the one or more previous mammogram is identified as potentially belonging to the patient using an identification not related to content of a mammogram image;

creating a match probability based on the comparison; and determining whether the one or more previous mammogram image belong to the patient using the match probability.

2. The method of claim 1, wherein the identification not related to content of a mammogram image is a patient name or a patient birthdate.

3. The method of claim 1, further comprising identifying that the one or more previous mammogram image belong to the patient and releasing the one or more mammogram image to an entity requesting for previously taken mammogram image of the patient.

4. The method of claim 3, wherein the one or more previous mammogram image is stored in a cloud storage.

5. The method of claim 4, wherein the one or more of the mammogram image includes a craniocaudal (CC) view of the pair of breasts.

6. The method of claim 4, wherein the one or more of the mammogram image includes a Mediolateral Oblique (MLO) view of the pair of breasts.

7. The method of claim 1, further comprising mapping one or more of the following on to a coordinate system: the first analysis result, the second analysis result; the third analysis result or the fourth analysis result.

8. The method of claim 7, wherein the comparison is based on the mapping.

9. A method for utilizing mammogram images for verification, comprising:

obtaining one or more mammogram image of a patient;

determining a first set of breast characteristics from the one or more mammogram image, wherein the first set of breast characteristics include breast landmark, breast tissue density, tissue pattern and breast finding;

comparing the first set of breast characteristics with a second set of breast characteristics to yield a comparison, wherein the second set of breast characteristics is from one or more previous mammogram image identified as potentially belonging to the patient using an identification not related to content of a mammogram image; and determining based on the comparison whether the one or more previous mammogram image belongs to the patient.

10. The method of claim 9, further comprising mapping the first set of breast characteristics on a coordinate system.

11. The method of claim 10, wherein the coordinate system includes horizontal rows and vertical rows, wherein one of the horizontal rows represent the location of a breast nipple and the horizontal rows above and below represent a corresponding fixed distance above and below the location of the breast nipple.

12. The method of claim 11, wherein each of the vertical rows represents a predetermined distance.

13. The method of claim 9, wherein the identification not related to content of a mammogram image is a patient name or a patient birthdate.

14. The method of claim 13, further comprising releasing the one or more mammogram image to an entity requesting for previously taken mammogram image of the patient.

15. The method of claim 9, wherein the comparison includes a probabilistic signature.

16. The method of claim 9, wherein the first set of breast characteristics further includes one or more of the following: surgical or biopsy clip, implant, skin lesion or artifact.

17. An apparatus comprising a processor and a memory, the memory containing program code executable by the processor for performing the following:

obtaining one or more mammogram image of a patient;

performing one or more of the following on the one or more mammogram image:
a) analyze nipple, skin line, and pectoralis muscle for assessment of size and shape of a breast or pair of breasts of the patient and generating a first analysis result;
b) analyze breast density and glandular pattern of the breast or pair of breasts of the patient and generating a second analysis result;
c) analyze at least one breast landmark and corresponding coordinate location of the at least one landmark and generating a third analysis result; or
d) analyze a region of greatest breast tissue density of the breast or pair of breasts of the patient and generating a fourth analysis result;

comparing one or more of the following to yield a comparison: the first analysis result, the second analysis result; the third analysis result or the fourth analysis result with one or more previous mammogram image, wherein the one or more previous mammogram is identified as potentially belonging to the patient using an identification not related to content of a mammogram image;

creating a match probability based on the comparison; and determining whether the one or more previous mammogram image belong to the patient using the match probability.

18. An apparatus comprising a processor and a memory, the memory containing program code executable by the processor for performing the following:

obtaining one or more mammogram image of a patient;

determining a first set of breast characteristics from the one or more mammogram image, wherein the first set of breast characteristics include breast landmark, breast tissue density, tissue pattern and breast finding;

comparing the first set of breast characteristics with a second set of breast characteristics to yield a comparison, wherein the second set of breast characteristics is from one or more previous mammogram image identified as potentially belonging to the patient using an identification not related to content of a mammogram image; and determining based on the comparison whether the one or more previous mammogram image belongs to the patient.

* * * * *